United States Patent
Möller

[11] Patent Number: 4,460,590
[45] Date of Patent: Jul. 17, 1984

[54] DIGLYCIDYL SUBSTITUTED HETEROCYCLIC COMPOUNDS

[75] Inventor: Hinrich Möller, Monheim, Fed. Rep. of Germany

[73] Assignee: Henkel Kommanditgesellschaft auf Aktien, Duesseldorf, Fed. Rep. of Germany

[21] Appl. No.: 391,476

[22] Filed: Jun. 23, 1982

[30] Foreign Application Priority Data

Aug. 7, 1981 [DE] Fed. Rep. of Germany ....... 3131365

[51] Int. Cl.$^3$ .................. A61K 31/505; C07D 487/04
[52] U.S. Cl. ..................................... 424/251; 424/253; 544/254; 544/256; 544/265; 544/280
[58] Field of Search ............... 544/254, 256, 280, 265; 424/251, 253

[56] References Cited
U.S. PATENT DOCUMENTS 4,343,940 8/1982 Kreighbaum et al. ............... 424/251
4,376,120 3/1983 Zeidler et al. ....................... 544/221

FOREIGN PATENT DOCUMENTS 0033503 12/1981 European Pat. Off. .
2907349 8/1980 Fed. Rep. of Germany .

*Primary Examiner*—Paul M. Coughlan, Jr.
*Attorney, Agent, or Firm*—Ernest G. Szoke; Henry E. Millson, Jr.

[57] ABSTRACT

Diclycidyl substituted heterocyclic compounds of the formula:

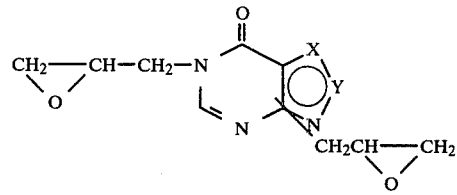

wherein X and Y can be the same or different and are either nitrogen or the radical C-R, where R is a hydrogen, or a hydrocarbon group, e.g., a straight or branched chain saturated or unsaturated hydrocarbon group, a substituted or unsubstituted cycloaliphatic group, an aromatic hydrocarbon-substituted alkyl group, a cycloaliphatic hydrocarbon-substituted alkyl group, an aromatic hydrocarbon group, a heterocyclic group, or a hetero-cyclic-substituted alkyl group, and where the glycidyl group in the five-membered ring is attached to a ring nitrogen atom; processes for their preparation; and compositions and methods for their use as cytostatic agents.

27 Claims, No Drawings

DIGLYCIDYL SUBSTITUTED HETEROCYCLIC COMPOUNDS

BACKGROUND OF THE INVENTION

German Patent DE-OS No. 29 07 349 discloses triglycidylisocyanurate and derivatives thereof which are useful as cytostatic agents in which each glycidyl group is bonded to a nitrogen atom in the isocyanurate ring structure and each nitrogen atom is present in the ring structure in amide form.

European Pat. No. 0 033 503 discloses N-heterocyclic compounds having at least two glycidyl substituted ring nitrogen atoms which are present in the ring structure in an amide or imide form. Such compounds exhibit highly effective tumor inhibiting properties.

DESCRIPTION OF THE INVENTION

The present invention relates to glycidyl substituted heterocyclic compounds containing two glycidyl groups, only one of which is attached to a ring nitrogen atom that is in the form of an amide structure with a neighboring carbonyl group.

The diglycidyl substituted heterocyclic compounds of the invention have the following general Formula I:

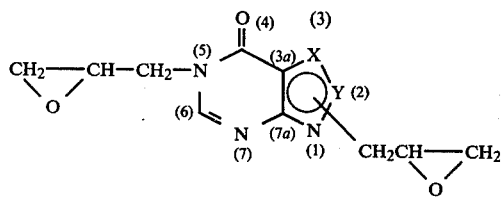

In the above Formula I, X and Y can be the same or different, and are either nitrogen or the radical C-R; the circle in the five-membered ring means that the five-membered ring is aromatic in nature; and the glycidyl group in the five-membered ring is attached to a ring nitrogen.

In the radical C-R in the above formula, R is hydrogen or a hydrocarbon radical. When the term "hydrocarbon radical" is used herein, it is understood to include radicals containing one or more heteroatoms, e.g. O, S, and P. The hydrocarbon radical contains from 1 to 12, preferably from 1 to 10, more preferably from 1 to 8, even more preferably from 1 to 6, and most preferably from 1 to 4 carbon atoms, chosen from the following:

(a) a straight or branched chain alkyl group, e.g. methyl, ethyl, propyl, butyl, pentyl, hexyl, octyl, decyl, dodecyl, isopropyl, isobutyl, 2-methylhexyl, 3-ethyloctyl, etc. The alkyl group may also contain from 1 to 3 oxygen or sulfur atoms, e.g. the alkyl group may contain one of the following moieties:

—CH$_2$—CH$_2$—O—CH$_2$—CH$_2$—, or
—CH$_2$—CH$_2$—O—CH$_2$CH$_2$—O—CH$_2$—CH$_2$—,
etc.

(b) a straight or branched chain unsaturated hydrocarbon radical, such as alkenyl or alkynyl, preferably an alkenyl radical, e.g. allyl, 1-butenyl, 2-butenyl, 2-methylallyl, 2-pentenyl, 1-octenyl, etc. The term "alkenyl" means an unsaturated aliphatic hydrocarbon which contains one or more double bonds and which may be straight or branched chain. The term "alkynyl" means an unsaturated aliphatic hydrocarbon containing one or more triple bonds, e.g. propargyl, butynyl, pentynyl, etc.

(c) a cycloaliphatic hydrocarbon group, preferably a 5- or 6-membered monocyclic group, e.g. cyclopentyl, cyclohexyl, etc.

(d) an aromatic hydrocarbon-substituted alkyl group, e.g. a phenylalkyl group wherein the alkyl group is a C$_1$–C$_6$ straight or branched chain alkyl group, such as benzyl, phenylethyl, 2-phenylisopropyl, 4-ethylbenzyl, 1-naphthylmethyl, etc.

(e) an aromatic hydrocarbon group, e.g. phenyl, naphthyl, tolyl, xylyl, etc.

(f) a heterocyclic group, preferably having a 5 or 6 membered ring, containing at least one of the following heteroatoms—O, N, P, or S, e.g. pyridyl, 2-pyridyl, or 3-pyridyl, pyrimidyl, pyrazolyl, imidazolyl, furyl, thienyl, oxazolyl, thiazolyl, piperidino, morpholino, thiomorpholino, etc. It should be noted that when the heteroatom is nitrogen, a hydrogen atom must not be present on the nitrogen atom, since an >N-H group will react with one of the glycidyl groups present in the compounds of Formula I.

(g) a cycloaliphatic hydrocarbon-substituted alkyl group, wherein the cycloaliphatic hydrocarbon moiety is preferably a 5- or 6-membered ring, and the alkyl group is a straight or branched chain alkyl group, e.g. cyclopentylmethyl, cyclohexylethyl, 2-cyclohexylisopropyl, etc.

(h) a heterocyclic-substituted alkyl group, wherein the heterocyclic moiety is as defined in (f) above, and the alkyl group is a straight or branched chain alkyl group, e.g. pyridylmethyl, pyridylethyl, 2-(2-pyridyl)-isopropyl, oxazolylbutyl, 2-thienylmethyl, 2-furylmethyl, etc.

When R contains an aromatic, cycloaliphatic, or heterocyclic moiety, such moiety is preferably monocyclic and may be unsubstituted, or may be substituted with from 1 to 3 straight or branched chain alkyl, alkenyl or alkynyl radicals, preferably containing from 1 to 4 carbon atoms, such as methyl, ethyl, propyl, butyl, isopropyl, isobutyl, allyl, 2-methylallyl, propargyl, butynyl, etc. R is preferably a straight or branched chain alkyl or unsaturated alkyl (e.g. alkenyl) group. It should be understood that the R group must be selected from groups that do not exhibit any significant reactivity with the epoxy portion of the glycidyl groups, since otherwise the compounds of Formula I will be unstable and without satisfactory shelf life on storage.

It should be noted that in the above Formula I, the glycidyl group in the five-membered ring can be attached to the nitrogen atom in the 1-position (the double bonds being in the 2, 3 and 3a, 7a positions); to a nitrogen atom in the 2-position, if a nitrogen atom is present in this position (the double bonds then being in the 1, 7a and 3, 3a positions); or to a nitrogen atom in the 3-position if a nitrogen atom is in fact present in this position (the double bonds then being in the 1, 2 and 3a, 7a positions).

Compounds of Formula I can be made by either of the following two processes, both starting with a compound of the general Formula II below. Compounds of Formula II and processes for their preparation are known from the literature and accordingly the starting materials of this invention can be prepared by those skilled in the art utilizing such known methods.

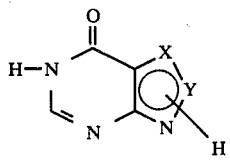

wherein X and Y have the same meanings as in Formula I above, and the hydrogen atom in the five-membered ring is attached to a ring nitrogen atom.

Process (A). The compound of Formula II is reacted with an epihalohydrin, such as epichlorohydrin or epibromohydrin. The reaction can take place in the presence of a small quantity of a basic catalyst, such as a tertiary amine or a quaternary ammonium compound, see, e.g. Houben-Weyl, "Methoden der Organic Chemie", Vol. 14/2 (1963), 497–547.

Process (B). The compound of Formula II is reacted with an allyl halide, such as allyl chloride or allyl bromide, to form a diallyl substituted compound of Formula III below:

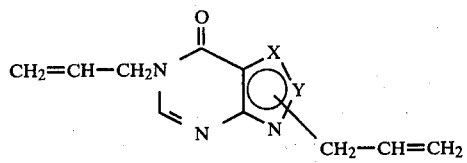

wherein X and Y have the meanings given for compounds of Formula I, and the allyl group in the five-membered ring is attached to a ring nitrogen atom.

The compound of Formula III is then reacted with a peracid to form a compound of Formula I. The reaction of an allyl halide with cyanuric acid is described in U.S. Pat. No. 3,376,301. The epoxidation of allyl isocyanurates with peracids is described in Houben-Weyl, Vol. 6/3, 385 et seq. The epoxidation step can be carried out in the presence of a small quantity of a quaternary ammonium compound as a catalyst. The same general methods set forth in the above references can be used for the two step process of Process (B).

The reaction of the heterocyclic compounds of Formula II with epihalohydrin or allylhalide is normally carried out at a temperature in the range of about 50° to about 150° C., preferably about 60° to about 110° C. The allyl halide or epihalohydrin is added in at least the required molar amount; however, excess amounts, for instance up to a molar ratio of about 30:1, can also be used.

A molar ratio in the range from about 5 to about 15 moles of allylhalide or epohalohydrin per mole of the compound of Formula II is particularly useful. The reaction can take place in a polar, aprotic solvent, which partially dissolves at least one of the reactants, and which does not react with the reactants. The reaction can also take place in the absence of a solvent. The preferred reaction time is from about 1 to about 10 hours, preferably about 2 to about 5 hours.

The epoxydation of the allyl groupings in compounds of Formula III with a peracid is also preferably carried out in the presence of a solvent. Here too, polar solvents are suitable, for instance a halogenated hydrocarbon or an alcohol. Suitable reaction temperatures for this step are in the range of about 0° to about 50° C., preferably between about 10° to about 30° C. The peracid is preferably used in approximately equivalent amounts or in slightly excess quantities. m-Chloroperbenzoic acid is commercially available and is suitable for use in this reaction. The reaction time is generally 24 hours or longer, for instance up to 48 hours.

Compounds of Formula I are then separated from the reaction mixture, and purified by known purification techniques, such as by elution from a chromatographic column.

The compounds of Formula I can be reacted with a primary or secondary diamine or with a dicarboxylic acid anhydride to form a polymer having a latice structure. Such polymers are useful in the same manner as known macromolecular epoxide resins, e.g. in sealants, adhesives, or as binders in paints. In addition when the compounds of Formula I are reacted with a polyamine such as ethylenediamine, the resulting reaction products can be used as ion exchangers.

The compounds of Formula I also exhibit cytostatic properties, and are useful in the treatment of various types of cancers, such as several types of leukemia, and against a number of malignant neoplasms, such as cancers of the lungs, cancers of the colon, melanoma, ependymoblastoma, and sarcoma. Also, the compounds of Formula I can be used in combination with known cytostatic agents, or in combination with other techniques useful in the treatment of the above malignancies.

The present invention also relates to pharmaceutical preparations containing a compound of Formula I, and to methods of inhibiting cell growth using the compounds of Formula I.

The compounds of Formula I can be formulated in finished unit dosage forms, e.g. capsules, tablets, sterile solutions for injection such as sterile isotonic solutions, etc., using known pharmaceutical adjuvant materials. Pharmaceutical adjuvant materials for oral dosage forms include, for example, inert diluents, such as calcium carbonate, sodium carbonate, lactose, calcium phosphate or sodium phosphate; granulating and disintegrating agents, for example, maize starch, gelatin or acacia; and lubricating agents, for example, magnesium stearate, stearic acid or talc. When tablet form is used, the tablets are preferably enteric coated to minimize any likelihood that hydrochloric acid in the stomach will affect the glycidyl radicals in the active compounds of the invention.

The finished unit dosage form is formulated to contain from about 1 to about 200 mg. of a compound of Formula I. The actual quantity of active compound chosen within the above range is dependent on the condition to be treated and the dosage frequency desired.

Mamalian patients to be treated with a compound of Formula I are administered a cytostatic (cell growth inhibiting) quantity of the compound of Formula I, either continuously, e.g. by intravenous drip at a rate sufficient to produce a cytostatic effect, or intermittently at convenient intervals using a unit dosage form thereof.

The invention will be better understood from the following examples, which are given for illustration purposes only and are not meant to limit the invention.

EXAMPLE I

Preparation of 1,5-diglycidyl-4-oxo-4,5-dihydro-pyrazolo[3,4-d]pyrimidine

A mixture of 13.6 g (0.1 mole) allopurinole, 185 g (2.0 mole) of epichlorohydrin, 0.6 g tetramethylammonium bromide, and 50 g of an 8 to 12 mesh grain size synthetic zeolite molecular sieve (0.4 mm) was stirred for 3 hours at 90°–95° C. and, after standing at room temperature overnight, mixed with 8.0 g (0.2 mole) powdered sodium hydroxide, stirred for 3 hours at 45° C., and then filtered. The filtrate was evaporated at 40° C. under reduced pressure, and the residue was chromatographically separated using silica gel (Merck). It was then eluted with methylene chloride containing 4% methanol.

From the fractions containing the substance with the highest $R_F$-value (DC-control), 9.6 g of 1,5-diglycidyl-4-oxo-4,5-dihydropyrazolo[3,4-d]pyrimidine were obtained after evaporating and vacuum drying. This product was a colorless, highly viscous liquid which crystallized after a period of time. Melting point 90°–95° C. Epoxide number: calculated 12.9; found 11.8.

EXAMPLE II

Using the isolated product of Example I, the following experiments were performed according to the testing procedures of the National Cancer Institute, Bethesda, Md. 20014, published in "Cancer Chemotherapy Reports", Part 3, September 1972, Vol. 3, No. 2. The above product was prepared immediately prior to application as a 1% aqueous solution for injection. Following the requirements of Protocol 1200 (Page 91C), mice in the number set forth in the Protocol were injected with Tumor Type P 388 (leukemia) intraperitoneally at $10^6$ cells/mouse. The average survival rate of the untreated animals was determined.

In further test groups according to the above Protocol, the above compound was injected into the mice. In a different series of tests, single doses of 200, 100, and 50 mg/kg body weight were administered. In all cases, a significant prolongation of life of the treated test animals, as compared to the average life expectancy of the animals that had not been treated with the active product had been achieved. The prolongation rate, T/C, in relation to the dosage of the active substance was as follows:

| Retardation of P 388-Tumor: | |
| --- | --- |
| mg/kg | T/C |
| 200 | 242 |
| 100 | 191 |
| 50 | 159 |

What is claimed is:

1. A diglycidyl-substituted heterocyclic compound of the formula:

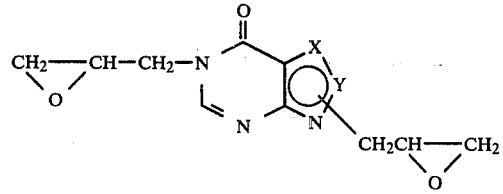

wherein the glycidyl group in the five-membered ring is attached to a ring nitrogen atom, and wherein X and Y are the same or different and are either nitrogen or the radical C-R, with R being hydrogen or a group containing from 1 to 12 carbon atoms selected from the following:

(a) a straight or branched chain alkyl group optionally containing from 1 to 3 oxygen or sulfur atoms;

(b) a straight or branched chain unsaturated hydrocarbon group;

(c) a cycloaliphatic hydrocarbon group;

(d) an aromatic hydrocarbon-substituted alkyl group;

(e) an aromatic hydrocarbon group;

(f) a heterocyclic group containing at least one heteroatom selected from the group consisting of O, N, P, and S, provided that when the heteroatom is nitrogen, the nitrogen atom is free of hydrogen atoms;

(g) a cycloaliphatic hydrocarbon-substituted alkyl group; and (h) a heterocyclic-substituted alkyl group wherein the heterocyclic moiety contains at least one heteroatom selected from the group consisting of O, N, P, and S, provided that when the heteroatom is nitrogen, the nitrogen atom is free of hydrogen atoms;

and wherein when R contains an aromatic, cycloaliphatic or heterocyclic moiety, such moiety may be unsubstituted or may be substituted with from 1 to 3 straight or branched chain alkyl, alkenyl, or alkynyl radicals.

2. A compound in accordance with claim 1 wherein the hydrocarbon group in (b) is an alkenyl or alkynyl group, the cycloaliphatic group in (c) and (g) contains a five- or six-membered ring, the aromatic hydrocarbon in (d) and (e) is phenyl or naphthyl, and the heterocyclic group in (f) and (h) contains a five- or six-membered ring.

3. A compound in accordance with claim 1 wherein R contains from 1 to 10 carbon atoms.

4. A compound in accordance with claim 1 wherein R contains from 1 to 8 carbon atoms.

5. A compound in accordance with claim 1 wherein R contains from 1 to 6 carbon atoms.

6. A compound in accordance with claim 1 wherein R is a straight or branched chain alkyl or alkenyl group.

7. A compound in accordance with claim 6 wherein R contains from 1 to 4 carbon atoms.

8. A compound in accordance with claim 1, 2, 3, 4, 5, 6, or 7 wherein X is nitrogen.

9. 1,5-diglycidyl-4-oxo-4,5-dihydro-pyrazolo[3,4-d]pyrimidine.

10. A pharmaceutical composition in finished dosage form comprising: (A) from about 1 to about 200 mg of a diglycidyl-substituted heterocyclic compound of the formula:

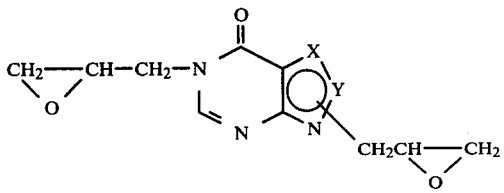

wherein the glycidyl group in the five membered ring is attached to a ring nitrogen atom, and wherein X and Y are the same or different and are either nitrogen or the radical C-R, with R being hydrogen or a group containing from 1 to 12 carbon atoms selected from the following:
(a) a straight or branched chain alkyl group optionally containing from 1 to 3 oxygen or sulfur atoms;
(b) a straight or branched chain unsaturated hydrocarbon group;
(c) a cycloaliphatic hydrocarbon group;
(d) an aromatic hydrocarbon-substituted alkyl group;
(e) an aromatic hydrocarbon group;
(f) a heterocyclic group containing at least one heteroatom selected from the group consisting of O, N, P, and S, provided that when the heteroatom is nitrogen, the nitrogen atom is free of hydrogen atoms;
(g) a cycloaliphatic hydrocarbon-substituted alkyl group; and
(h) a heterocyclic-substituted alkyl group wherein the heterocyclic moiety contains at least one heteroatom selected from the group consisting of O, N, P, and S, provided that when the heteroatom is nitrogen, the nitrogen atom is free of hydrogen atoms;
and wherein when R contains an aromatic, cycloaliphatic or heterocyclic moiety, such moiety may be unsubstituted or may be substituted with from 1 to 3 straight or branched chain alkyl, alkenyl, or alkynyl radicals; and (B) pharmaceutical adjuvant material.

11. A composition in accordance with claim 10 wherein the hydrocarbon group in (b) is an alkenyl or alkynyl group, the cycloaliphatic group in (c) and (g) contains a five- or six-membered ring, the aromatic hydrocarbon in (d) and (e) is phenyl or naphthyl, and the heterocyclic group in (f) and (h) contains a five- or six-membered ring.

12. A composition in accordance with claim 10 wherein R contains from 1 to 10 carbon atoms.

13. A composition in accordance with claim 10 wherein R in said compound contains from 1 to 8 carbon atoms.

14. A composition in accordance with claim 10 wherein R in said compound contains from 1 to 6 carbon atoms.

15. a composition in accordance with claim 10 wherein R in said compound is a straight or branched chain alkyl or alkenyl group.

16. A composition in accordance with claim 15 wherein R in said compound contains from 1 to 4 carbon atoms.

17. A composition in accordance with claim 10, 11, 12, 13, 14, 15, or 16 wherein X in said compound is nitrogen.

18. A composition in accordance with claim 10 wherein said compound is 1,5-diglycidyl-4-oxo-4,5-dihydro-pyrazolo[3,4-d]pyrimidine.

19. A method of inhibiting cell growth in a mammal comprising treating said mammal with a cell growth-inhibiting quantity of a diglycidyl-substituted heterocyclic compound of the formula:

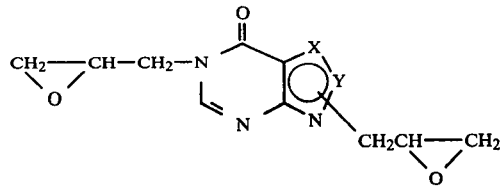

wherein the glycidyl group in the five-membered ring is attached to a ring nitrogen atom, and wherein X and Y are the same or different and are either nitrogen or the radical C-R, with R being hydrogen or a group containing from 1 to 12 carbon atoms selected from the following:
(a) a straight or branched chain alkyl group optionally containing from 1 to 3 oxygen or sulfur atoms;
(b) a straight or branched chain unsaturated hydrocarbon group;
(c) a cycloaliphatic hydrocarbon group;
(d) an aromatic hydrocarbon-substituted alkyl group;
(e) an aromatic hydrocarbon group;
(f) a heterocyclic group containing at least one heteroatom selected from the group consisting of O, N, P, and S, provided that when the heteroatom is nitrogen, the nitrogen atom is free of hydrogen atoms;
(g) a cycloaliphatic hydrocarbon-substituted alkyl group; and
(h) a heterocyclic-substituted alkyl group wherein the heterocyclic moiety contains at least one heteroatom selected from the group consisting of O, N, P, and S, provided that when the heteroatom is nitrogen, the nitrogen atom is free of hydrogen atoms;
and wherein when R contains an aromatic, cycloaliphatic or heterocyclic moiety, such moiety may be unsubstituted or may be substituted with from 1 to 3 straight or branched chain alkyl, alkenyl, or alkynyl radicals.

20. A method in accordance with claim 19 wherein the hydrocarbon group in (b) is an alkenyl or alkynyl group, the cycloaliphatic group in (c) and (g) contains a five- or six-membered ring, the aromatic hydrocarbon in (d) and (e) is phenyl or naphthyl, and the heterocyclic group in (f) and (h) contains a five- or six-membered ring.

21. A method in accordance with claim 19 wherein R in said compound contains from 1 to 10 carbon atoms.

22. A method in accordance with claim 19 wherein R in said compound contains from 1 to 8 carbon atoms.

23. A method in accordance with claim 19 wherein R in said compound contains from 1 to 6 carbon atoms.

24. A method in accordance with claim 19 wherein R in said compound is a straight or branched chain alkyl or alkenyl group.

25. A method in accordance with claim 24 wherein R contains from 1 to 4 carbon atoms.

26. A method in accordance with claim 19, 20, 21, 22, 23, 24, or 25 wherein X is nitrogen.

27. A method in accordance with claim 19 wherein said compound is 1,5-diglycidyl-4-oxo-4,5-dihydropyrazolo[3,4-d]pyrimidine.

* * * * *